United States Patent [19] [11] 4,055,565
Hotta et al. [45] Oct. 25, 1977

[54] OPTICAL BRIGHTENING AGENTS OF NAPHTHALIMIDE DERIVATIVES

[75] Inventors: Seiji Hotta, Hirakata; Takashi Akamatsu, Ashiya, both of Japan

[73] Assignee: Sumitomo Chemical Company, Limited, Osaka, Japan

[21] Appl. No.: 385,578

[22] Filed: Aug. 3, 1973

Related U.S. Application Data

[62] Division of Ser. No. 100,816, Dec. 22, 1970, Pat. No. 3,798,224.

[30] Foreign Application Priority Data

Dec. 30, 1969 Japan .................................. 45-1862
Dec. 30, 1969 Japan .................................. 45-1863
Dec. 30, 1969 Japan .................................. 45-1864
Dec. 30, 1969 Japan .................................. 45-1865
Dec. 30, 1969 Japan .................................. 45-1866
May 8, 1970 Japan .................................. 45-39536
May 23, 1970 Japan .................................. 45-44291
July 15, 1970 Japan .................................. 45-62427
Sept. 18, 1970 Japan .................................. 45-82103
Sept. 18, 1970 Japan .................................. 45-82104
Nov. 6, 1970 Japan .................................. 45-98113
Nov. 12, 1970 Japan .................................. 45-100011
Nov. 12, 1970 Japan .................................. 45-100012
Nov. 12, 1970 Japan .................................. 45-100013

[51] Int. Cl.² .................................. C07D 217/24
[52] U.S. Cl. .................. 260/281 N; 260/281 NH; 260/281 S; 260/250 Q; 260/250 P; 260/256.4 B; 260/256.4 R; 260/256.5 R; 252/301.2; 252/6; 106/288 Q; 8/1 D; 8/1 W
[58] Field of Search .......................... 260/281, 281 N; 252/301.2 W, 301.3 W

[56] References Cited

U.S. PATENT DOCUMENTS 3,310,564 3/1967 Kasai .................................. 260/281
3,330,834 7/1967 Senshu .................................. 260/281
3,467,600 8/1969 Zweidler .................................. 260/301.2 W
3,880,857 4/1975 Scheuerman .................................. 260/281 N

OTHER PUBLICATIONS

Onishi et al., Nippon Kagaku Zasshi 88, 1221, (1967).

Primary Examiner—Alton D. Rollins
Assistant Examiner—Mark L. Berch
Attorney, Agent, or Firm—Stevens, Davis, Miller & Mosher

[57] ABSTRACT

A naphthalimide derivative having the formula

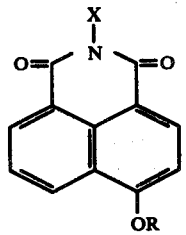

wherein
R is an alkyl, or cycloalkyl, an aralkyl, a haloalkyl, an alkoxyalkyl, a hydroxyalkyl, an N,N-dialkylaminoalkyl, an unsubstituted or halogen-, alkyl-, alkoxy- or hydroxy-substituted aryl, or an ammoniumalkyl; X is a group of the formula,

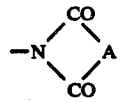

wherein A is

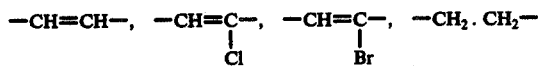

or an unsubstituted or halogen-substituted arylene, or a group of the formula,

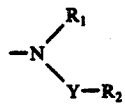

wherein $R_1$ is hydrogen, an alkyl, phenyl, a hydroxyalkyl, or an alkoxyalkyl; Y is —CO—, —COO—, —CONR₃— (where $R_3$ is hydrogen or an alkyl), or —SO₂—; $R_2$ is hydrogen, an alkyl, a cycloalkyl, an aralkyl, a haloalkyl, an alkyl- or aryl-substituted amino-alkyl, an unsubstituted or halogen-, alkyl-, alkoxy-, hydroxy-, amino- or alkylamino-substituted aryl, a group of the formula,

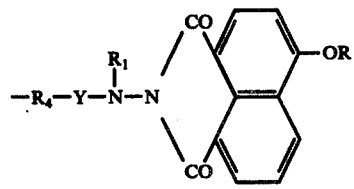

(where R, $R_1$ and Y are as defined above and $R_4$ is a bivalent group), or a group of the formula,

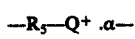

(where $R_5$ is direct linkage or a bivalent group; $Q^+$ is a substituted ammonium, a cycloammonium or a hydrazinium; and $\alpha^-$ is an anion),
which is useful for optically brightening an organic polymer material.

11 Claims, No Drawings

OPTICAL BRIGHTENING AGENTS OF NAPTHALIMIDE DERIVATIVES

This is a division, of application Ser. No. 100,816, filed Dec. 22, 1970, now U.S. Pat. No. 3,798,224.

This invention relates to novel naphthalimide compounds and to a process for optically brightening organic polymers with the compounds.

This invention provides a novel naphthalimide compound represented by the formula, (I)

wherein
R is an alkyl, a cycloalkyl, an aralkyl, a haloalkyl, an alkoxyalkyl, a hydroxyalkyl, an N,N-dialkylaminoalkyl, an unsubstituted or halogen-, alkyl-, alkoxy- or hydroxy-substituted aryl, or an ammoniumalkyl; X is a group of the formula, wherein A is —CH=CH—, —CH=C—, —CH=C—, —CH$_2$·CH$_2$—
    |        |
    Cl      Br or an unsubstituted or halogen-substituted arylene, or a group of the formula, wherein R$_1$ is hydrogen, an alkyl, phenyl, a hydroxyalkyl, or an alkoxy-alkyl; Y is —CO—, —COO—, —CONR$_3$— (where R$_3$ is hydrogen or an alkyl), or —SO$_2$—; R$_2$ is hydrogen, an alkyl, a cycloalkyl, an aralkyl, a haloalkyl, an alkyl- or aryl-substituted aminoalkyl, an unsubstituted or halogen-, alkylalkoxy-, hydroxy-, amino- or alkylamino-substituted aryl, a group of the formula, (where R, R$_1$ and Y are as defined above and R$_4$ is a bivalent group), or a group of the formula, —R$_5$—Q$^+$·a$^-$—

(where R$_5$ is direct linkage or a bivalent group; Q$^+$ is a substituted ammonium, a cycloammonium or a hydrazinium; and a$^-$ is an anion).

The term, "alkyl," used in the present specification means an alkyl having 1 to 6 carbon atoms.

Also, a bivalent group represented by R$_5$ is exemplified by an aliphatic chain such as an unsubstituted or halogen- or alkyl-substituted alkylene (C$_1$-C$_3$),

—CH$_2$NHCH$_2$CH$_2$—

—CH$_2$CH$_2$SO$_2$CH$_2$CH$_2$—,

—CH=CH·CH$_2$—, etc.; an unsubstituted or alkyl-, N-alkylcarbamoyl-, amido- or phenoxyimido-substituted phenylene such as

, —CH$_2$—,

—CONHCH$_2$CH$_2$CH$_2$—

—NHCOCH$_2$—,

—O— —NHCOCH$_2$— etc, or a heterocyclic ring such as

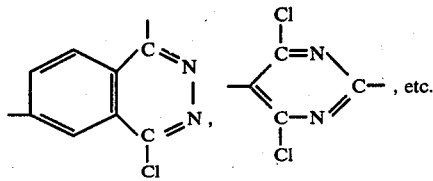

This invention also provides a process for preparing the naphthalimide compound having the Formula I, which comprises (1) reacting a compound of the formula,

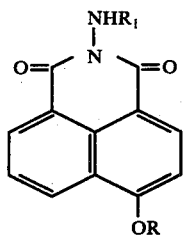
(II)

wherein R and R₁ are as defined above, with a cyanate, an isocyanic acid derivative, an acid halide of the formula,

R₂—Y—Z        (III)

or

Z—Y—R₄—Y—Z   (IV)

or an acid anhydride of the formula,

R₂—Y—O—Y—R₂  (V)

or

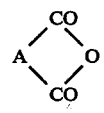
(VI)

(in the above formulas, Z is halogen and R₂R₄, Y and A are as defined above), or (2) reacting a compound of the formula,

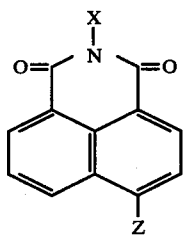
(VII)

wherein X and Z are as defined above, with a compound of the formula,

ROH        (VIII)

wherein R is as defined above, or (3) reacting a compound of the formula,

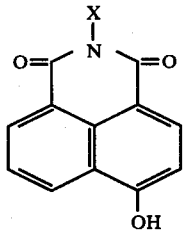
(IX)

wherein X is as defined above, with an alkylating agent, or (4) reacting a compound of the formula,

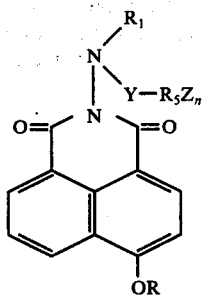
(X)

wherein R₁, R₅, Y and Z are as defined above and n is an integer of 1 or 2 or the formula,

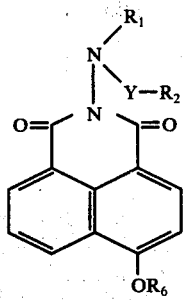
(XI)

wherein R₆ is a haloalkyl and R₁, R₂ and Y are as defined above, with an amine or hydrazine and then reacting the resulting naphthalimide derivative with an alkylating agent or a quaternizing agent, if necessary.

The present invention is explained below in more detail.

PROCESS (1)

Examples of a compound of the Formula II are as follows:
N-amino-4-methoxynaphthalimide
N-amino-4-butoxynaphthalimide
N-amino-4-(2-methoxyethoxy)naphthalimide
N-amino-4-(2-ethoxyethoxy)naphthalimide
N-amino-4-(2-butoxyethoxy)naphthalimide N-amino-4(3-chloro-2-hydroxypropoxy)naphthalimide
N-amino-4-benzyloxynaphthalimide
N-amino-4-phenoxynaphthalimide
N-amino-4-(p-methylphenoxy)naphthalimide
N-amino-4-(p-chlorophenoxy)naphthalimide
N-amino-4-(p-methoxyphenoxy)naphthalimide
N-amino-4-(m-methylphenoxy)naphthalimide
N-methylamino-4-methoxynaphthalimide
N-methylamino-4-ethoxynaphthalimide
N-methylamino-4-propoxynaphthalimide
N-methylamino-4-butoxynaphthalimide
N-methylamino-4-isopropoxynaphthalimide
N-amino-4-ethoxynaphthalimide
N-amino-4-propoxynaphthalimide
N-methylamino-4-isobutoxynaphthalimide
N-methylamino-4-benzyloxynaphthalimide
N-methylamino-4-phenoxynaphthalimide
N-methylamino-4-(p-chlorophenoxy)naphthalimide
N-methylamino-4-(m-methylphenoxy)naphthalimide
N-methylamino-4-(p-methoxyphenoxy)napthalimide
N-methylamino-4-(2-naphthyloxy)naphthalimide
N-methylamino-4-(2-methoxyethoxy)naphthalimide
N-methylamino-4-(2-ethoxyethoxy)naphthalimide
N-methylamino-4-(2-butoxyethoxy)naphthalimide
N-methylamino-4-(2-hydroxyethoxy)naphthalimide
N-methylamino-4-(3-chloro-2-hydroxypropoxy) naphthalimide
N-ethylamino-4-methoxynaphthalimide
N-ethylamino-4-ethoxynaphthalimide
N-ethylamino-4-butoxynaphthalimide
N-ethylamino-4-benzyloxynaphthalimide
N-ethylamino-4-phenoxynaphthalimide
N-ethylamino-4-(m-methoxyphenoxy)naphthalimide
N-ethylamino-4-(o-methylphenoxy)naphthalimide
N-ethylamino-4-(2,4-dimethylphenoxy)naphthalimide
N-ethylamino-4-(2-methoxyethoxy)naphthalimide
N-ethylamino-4-(2-butoxyethoxy)naphthalimide
N-ethylamino-4-(2-diethylaminoethoxy)naphthalimide
N-propylamino4-methoxynaphthalimide
N-propylamino-4-ethoxynaphthalimide
N-propylamino-4-propoxynaphthalimide
N-propylamino-4-butoxynaphthalimide
N-propylamino-4-phenoxynaphthalimide
N-propylamino-4-(2-methoxyethoxy)naphthalimide
N-propylamino-4-(2-butoxyethoxy)naphthalimide
N-butylamino-4-methoxynaphthalimide
N-butylamino-4-ethoxynaphthalimide
N-butylamino-4-butoxynaphthalimide
N-butylamino-4-phenoxynaphthalimide
N-butylamino-4-(2-methoxyethoxy)naphthalimide
N-(2-hydroxyethylamino)-4-methoxynaphthalimide
N-(2-hydroxyethylamino)-4-ethoxynaphthalimide
N-(2-hydroxyethylamino)-4-butoxynaphthalimide
N-(2-hydroxyethylamino)-4-phenoxynaphthalimide
N-(2-thydroxyethylamino)-4-(2-methoxyethoxy) naphthalimide
N-(2-hydroxyethylamino)-4-(2-butoxyethoxy) naphthalimide
N-(2-hydroxyethylamino)-4-(p-hydroxyphenoxy) naphthalimide
N-(2-methoxyethylamino)-4-methoxynaphthalimide
N-(2-methoxyethylamino)-4-ethoxynaphthalimide
N-(2-methoxyethylamino)-4-phenoxynaphthalimide
N-(2-methoxyethylamino)-4-(2-methoxyethoxy) naphthalimide
N-(2-ethoxyethylamino)-4-methoxynaphthalimide
N-(2-ethoxyethylamino)-4-ethoxynaphthalimide
N-(2-ethoxyethylamino)-4-phenoxynaphthalimide
N-(2-ethoxyethylamino)-4-(2-ethoxyethoxy) naphthalimide
N-(2-ethoxyethylamino)-4-(2-butoxyethoxy) naphthalimide Examples of a cyanate and an isocyanic acid derivative are as follows:
Hexamethylene diisocyanate
Potassium cyanate
Methyl isocyanate
Ethyl isocyanate
Propyl isocyanate
Butyl isocyanate
Cyclonexyl isocyanate
Phenyl isocyanate
p-Tolyl isocyanate
Benzyl isocyanate
Toluylene diisocyanate
Xylylene diisocyanate
Hexamethylene diisocyanate Examples of an acid halide of the Formula III or IV are as follows:
Acetyl chloride
Acetyl bromide
Acetyl iodide
Chloroacetyl chloride
Bromoacetyl chloride
Propionyl chloride
Butyryl chloride
Isobutyryl chloride
Cyclohexane carbonyl chloride
Benzoyl chloride
Benzoyl bromide
p-Anisoyl chloride
p-Chlorobenzoyl chloride
m-Chlorobenzoyl chloride
o-Chlorobenzoyl chloride
2,4-dichlorobenzoyl chloride
p-Toluyl chloride
m-Toluyl chloride
o-Toluyl chloride
Terephthaloyl dichloride
Isophthaloyl dichloride
Fumaroyl dichloride
Malonyl dichloride
Succinyl dichloride
Adipoyl dichloride
Acryloyl chloride
Methacryloyl chloride
Cinnamoyl chloride
Furoyl chloride
Nicotinyl chloride
Methyl chloroformate
Ethyl chloroformate
Phenyl chloroformate
Dimethylcarbamoyl chloride
Diethylcarbamoyl chloride
Methanesulfonyl chloride
Ethanesulfonyl chloride
Ethanesulfonyl bromide
Benzenesulfonyl chloride
Tosyl chloride
p-Chlorobenzenesulfonyl chloride
1,3-benzenedisulfonyl dichloride
4-chloro-1,3-benzenedisulfonyl dichloride Examples of an acid anhydride of the Formula V or VI are as follows:
Acetic anhydride
Propionic anhydride Butyric anhydride
Isobutyric anhydride
Valeric anhydride
Hexanoic anhydride
Cyclohexanecarboxylic anhydride
Benzoic anhydride
Succinic anhydride
Maleic anhydride
Phthalic anhydride
Naphthalic anhydride
Dichlorophthalic anhydride
Tetrachlorophthalic anhydride
Trimellitic anhydride
Pyromellitic anhydride The present Compound I may be obtained by heating a mixture of a compound of the Formula II with a cyanate or an isocyanic acid derivative or a compound of the Formula III, IV, V or VI at a suitable temperature within a range from 0° to 200° C. in the presence or absence of water, acetic acid or an alcoholic solvent such as metanol, ethanol, etc, a ketone solvent such as acetone, methyl isobutyl ketone, etc., an aromatic solvent such as benzene, toluene, chlorobenzene, etc, or an amide solvent such as dimethylformamide, dimethylacetamide, etc. or a mixture thereof. If necessary, acid binding agent such as sodium hydroxide, sodium carbonate, potassium acetate, triethylamine or pyridine may be used.

PROCESS (2)

Examples of a compound of the Formula VIII are as follows:
N-acetylamino-4-chloronaphthalimide
N-benzoylamino-4-chloronaphthalimide
N-toluylamino-4-chloronaphthalimide
N-propionylamino-4-chloronaphthalimide
N-butyrylamino-4-chloronaphthalimide
N-(p-chlorobenzoyl)amino-4-chloronaphthalimide
N-(o-chlorobenzoyl)amino-4-chloronaphthalimide
N-phthalinido-4-chloronaphthalimide
N-dichlorophthalimido-4-chloronaphthalimide
N-naphthalimido-4-chloronaphthalimide
N-acetylamino-4-bromonaphthalimide
N-benzoylamino-4-bromonaphthalimide
N-(methylacetylamino)-4-chloronaphthalimide
N-(methylacetylamino)-4-bromonaphthalimide
N-(ethylacetylamino)-4-chloronaphthalimide
N-(ethylacetylamino)-4-bromonaphthalimide
N-(propylacetylamino)-4-chloronaphthalimide
N-(butylacetylamino)-4-chloronaphthalimide
N-(2-hydroxyethylacetylamino)-4-chloronaphthalimide
N-(methylpropionylamino)-4-chloronaphthalimide
N-(methylbutyrylamino)-4-chloronaphthalimide
N-(ethylbutyrylamino)-4-chloronaphthalimide
N-(methylcyclohexanecarbonylamino)-4-chloronaphthalimide
N-(methylbenzoylamino)-4-chloronaphthalimide
N-(ethylbenzoylamino)-4-chloronaphthalimide
N-(ethylbenzoylamino)-4-bromonaphthalimide
N-(propylbenzoylamino)-4-bromonaphthalimide
N-(butylbenzoylamino)-4-bromonaphthalimide
N-(2-methoxybenzoylamino)-4-chloronaphthalimide
N-(methyl-p-toluylamino)-4-bromonaphthalimide
N-(ethyl-p-toluylamino)-4-bromonaphthalimide
N-(methyl-m-toluylamino)-4-chloronaphthalimide
N-(methyl-o-toluylamino)-4-chloronaphthalimide
N-(methyl-p-chlorobenzoylamino)-4-chloronaphthalimide
N-(ethyl-p-chlorobenzoylamino)-4-chloronaphthalimide
N-(methyl-2,4-dichlorobenzoylamino)-4-bromonaphthalimide
N-(methylanisoylamino)-4-bromonaphthalimide
N-(methylacryloylamino)-4-bromonaphthalimide Examples of a compound of the Formula VII are as follows:
Methanol
Ethanol
Propanol
2-propanol
Butanol
Isobutyl alcohol
Allyl alcohol
Benzyl alcohol
Phenethyl alcohol
Ethylene glycol
Propylene glycol
2-methoxyethyl alcohol
2-ethoxyethyl alcohol
2-butoxyethyl alcohol
2-diethylaminoethyl alcohol
Phenol
o-Cresol
m-Cresol
p-Cresol
p-Methoxyphenol
m-Methoxyphenol
Xylenol
p-Chlorophenol
o-Chlorophenol
2,4-dichlorophenol
2-naphthol
Hydroquinone
Resorcinol The compound of the Formula I may be obtained by stirring the mixture of a compound of the Formula VII with a compound of the Formula VIII at a temperature of 30° to 250° C. and preferably of 50° to 150° C. using an excess amount of the compound of the Formula VIII as a solvent. It is preferred to add potassium hydroxide or sodium hydroxide as an acid binding agent. If necessary, the reaction may be carried out in the presence of an inert solvent.

PROCESS (3)

Examples of a compound of the Formula IX are as follows:
N-acetylamino-4-hydroxynaphthalimide
N-(methylacetylamino)-4-hydroxynapthalimide
N-(ethylacetylamino)-4-hydroxynaphthalimide
N-(butylacetylamino)-4-hydroxynaphthalimide
N-(2-methoxyethylacetylamino)-4-hydroxynaphthalimide
N-benzoylamino-4-hydroxynaphthalimide
N-(methylbenzoylamino)-4-hydroxynaphthalimide
N-(ethylbenzoylamino)-4-hydroxyanphthalimide
N-(p-chlorobenzoylamino)-4-hydroxynaphthalimide
N-(p-toluylamino)-4-hydroxynaphthalimide
N-(methyl-p-toluylamino)-4-hydroxynaphthalimide
N-(ethyl-p-toluylamino)-4-hydroxynaphthalimide
N-ureido-4-hydroxynaphthalimide
N-(3-methylureido)-4-hydroxynaphthalimide
N-(3-phenylureido)-4-hydroxynaphthalimide
N-(1,3-dimethylureido)-4-hydroxynaphthalimide
N-ethoxycarbonylamino-4-hydroxynaphthalimide
N-phenoxycarbonylamino-4-hydroxynaphthalimide N-tosylamino-4-hydroxynaphthalimide Examples of the alkylating agent include a halogenated alkyl such as
  methyl chloride
  methyl bromide
  methyl iodide
  ethyl chloride
  ethyl bromide
  ethylene dibromide
  propyl chloride
  butyl bromide
  benzyl chloride
  benzyl bromide
  ethylene chlorohydrin
an ester such as
  dimethyl sulfate
  diethyl sulfate
  dibutyl sulfate
  methyl p-toluenesulfonate
  ethyl p-toluenesulfonate
  butyl p-toluenesulfonate
  2-methoxyethyl p-toluenesulfonate
  2-ethoxyethyl p-toluenesulfonate
  2-butoxyethyl p-toluenesulfonate
an epoxy ring-containing compound such as
  ethylene oxide
  propylene oxide, or
  epichlorohydrin
or an active vinyl group-containing compound such as
  acrylonitrile, or
  acrylamide A condensation may be accomplished by stirring the mixture of the compound of the Formula IX and the alkylating agent in an aqueous solvent at a temperature of 0° to 150° C., if necessary, by the addition of sodium hydroxide, potassium hydroxide, sodium carbonate or sodium acetate.

PROCESS (4)

A halogenated compound of the formula X or XI can be produced by the processes (1), (2) or (3) as described above.

Examples of the compound of the Formula X or XI are as follows:

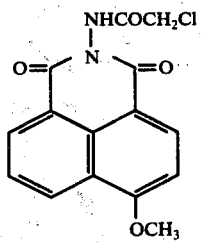

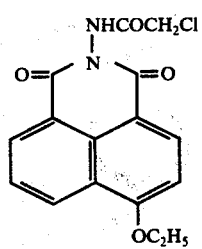

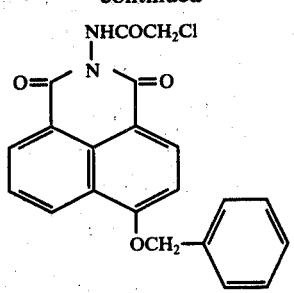

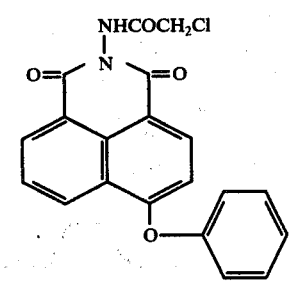

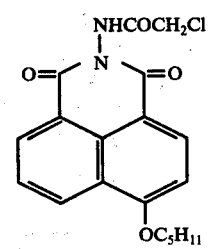

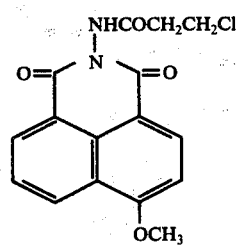

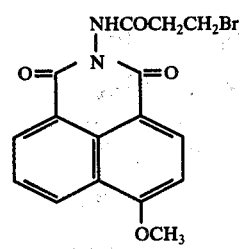

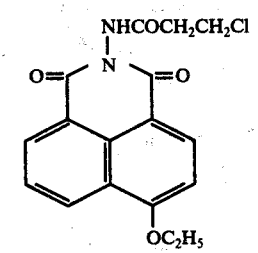

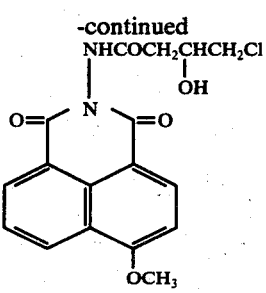
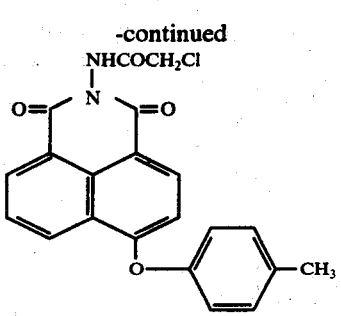
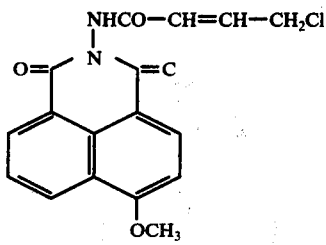
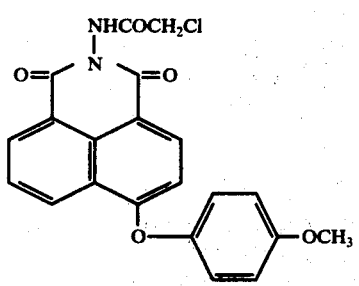
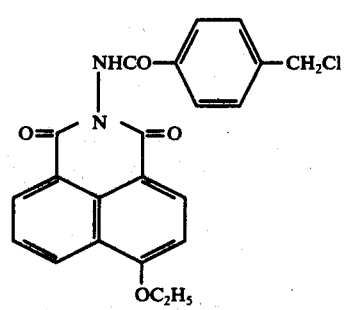
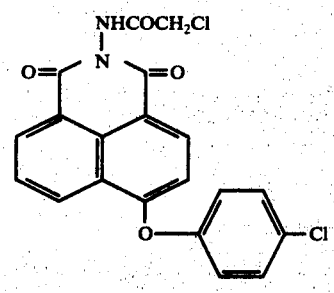
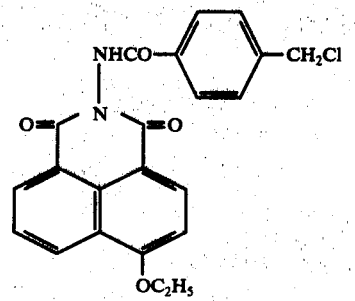
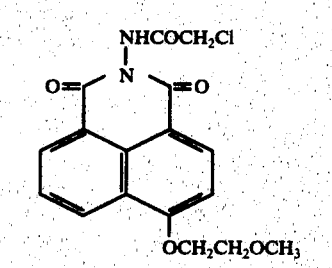
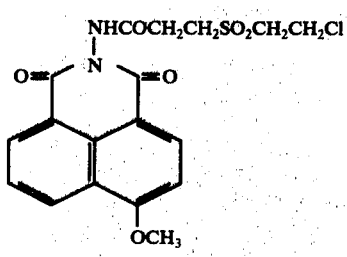
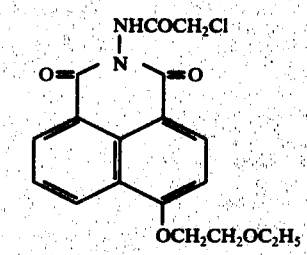
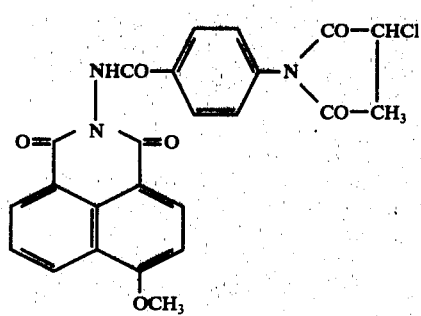
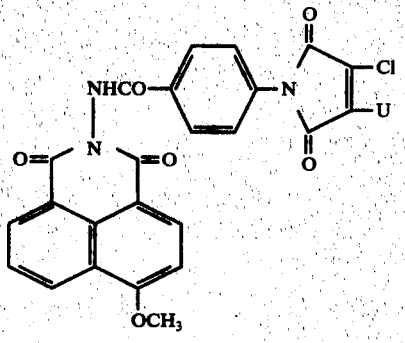

-continued
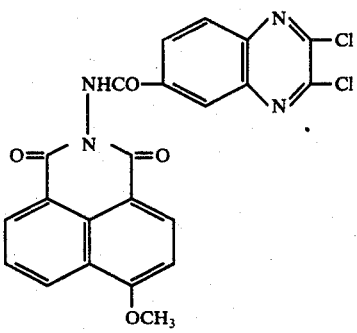
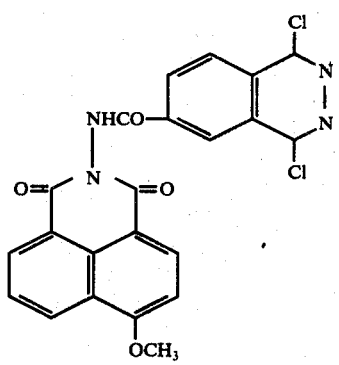
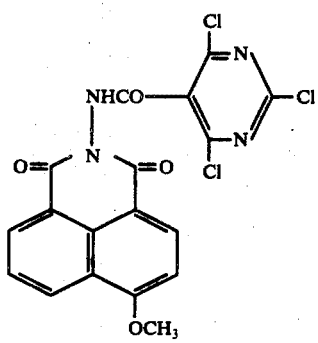
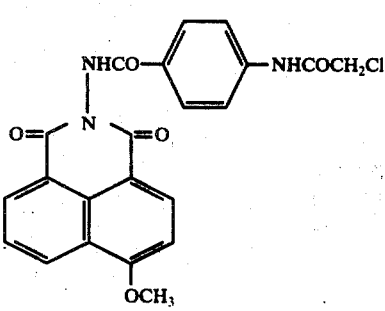
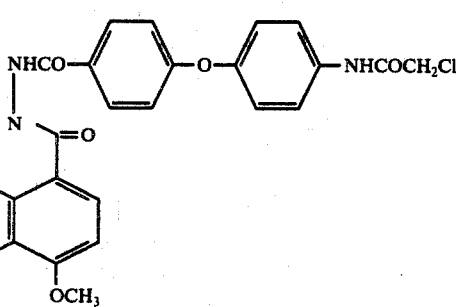
-continued
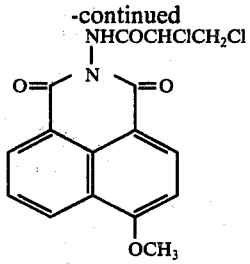
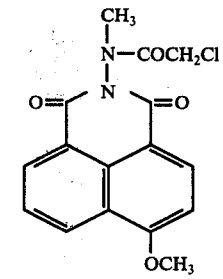
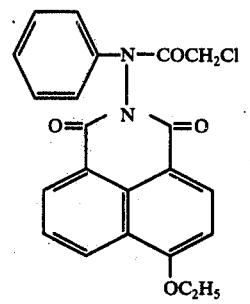
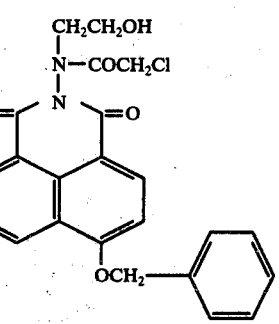
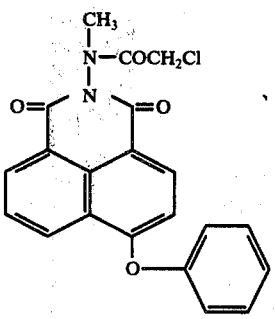
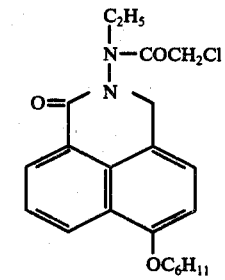

-continued
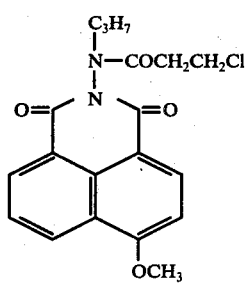
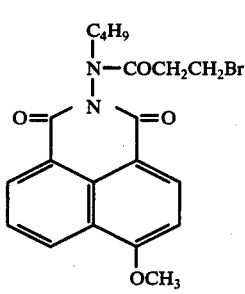
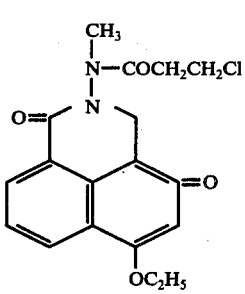
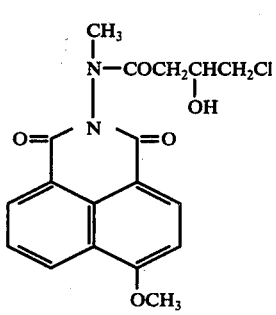
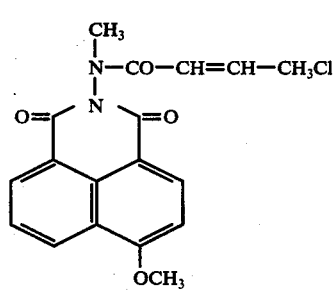
-continued
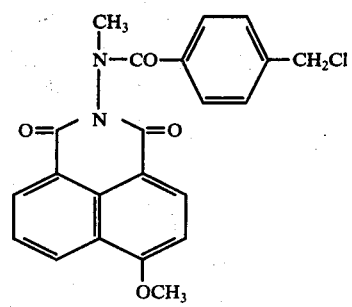
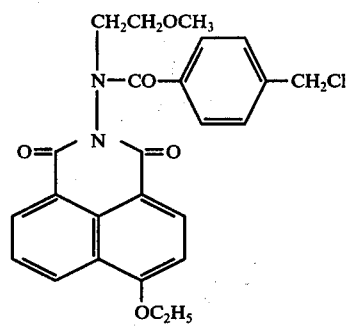
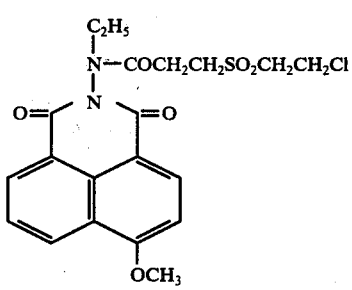
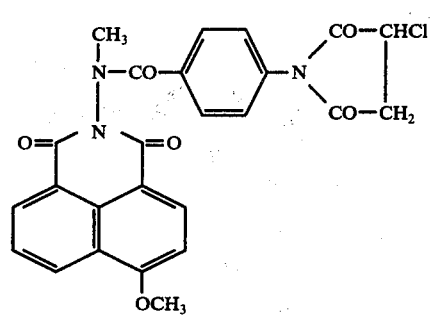
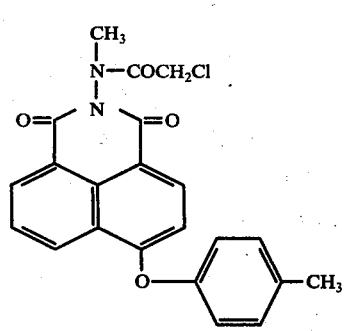

-continued
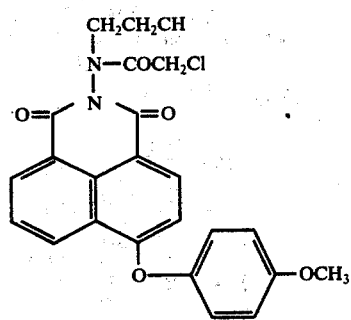
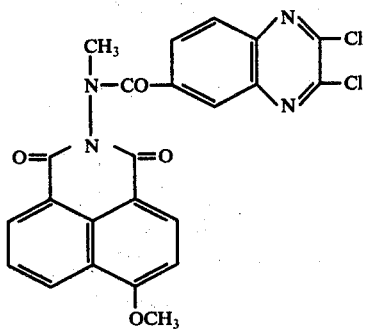

-continued

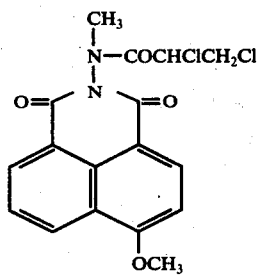

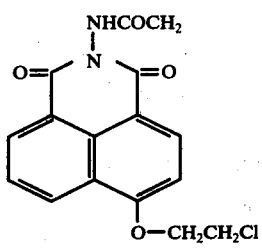

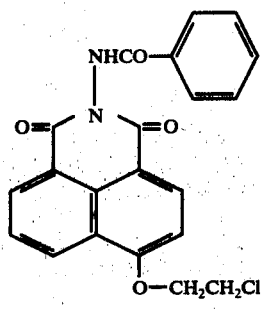

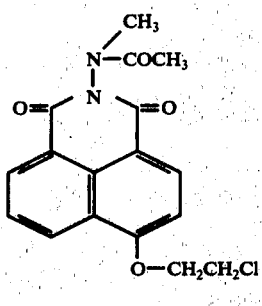

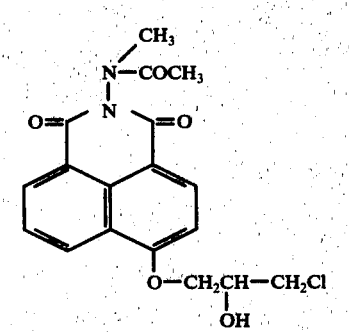

-continued

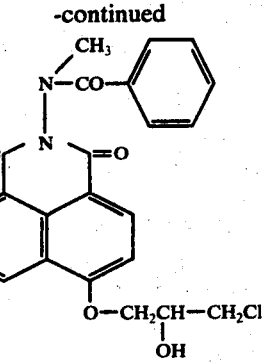

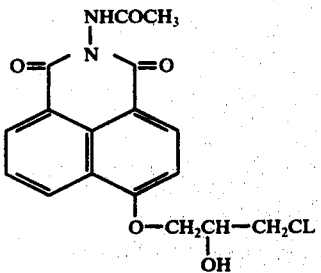

As the amine, tertiary, secondary and primary amines and ammonia may be used. Examples of tertiary amines are as follows:
Trimethlamine
Triethylamine
Diethylmethylamine
Diethanolmethylamine
Bis($\beta$-cyanioethyl)methyalmine
Dimethylcyclohexylamine
N-methylyrrolidine
N-methylpiperidine
N-methylmorpholine
Dimethylaniline
Pyridine
Picoline
Quinoline
Triethylenediamine Examples of secondary amines are as follows:
Dimethylamine
Diethylamine
Diethanolamine
Pyrrolidine
Piperidine
Morpholine
N-methylaniline Examples of primary amines are alkylamines such as
methylamine
ethylamine
n-propylamine
n-butylamine, etc.
cycloalkylamines such as cyclohexylamine, etc.
aralkylamines such as benzylamine, etc.
and aromatic amnes such as aniline
toluidine
anisidine
naphthylamines, etc.
diamines such as ethylenediamine
1,3-propanediamine
phenylenediamine, and
4,4'-diaminodihenyl ether Examples of hydrazine derivatives are hydrazine, hydrazine hydrate, methylhydrazine, ethylhydrazine, N,N-dimethylhydrazine, N-methyl-N-phenylhydrazine, N-aminopyrrolidine, phenylhydrazine, p-chlorophenylhydrazine and various salts thereof such as hydrochloride, sulfate, etc. thereof.

A reaction of an active halogen atom-containing naphthalimide of the Formula X or XI with an amine may be accomplished at a temperature of 0° to 150° C. in the presence or absence of a solvent. If necessary the reaction may be carried out at elevated pressures although it is usually carried out at normal pressure. As a solvent, water, alcohols such as methanol, ethanol, etc., ketones such as acetone, methyl isobutyl ketone, etc., ethers such as ethyl ether, dioxane, etc., dimethylformamide or dimethylsulfoxide and aromatic solvents such as benzene, toluene, chlorobenzene, etc. and mixtures thereof may be used.

Thus, naphthalimide compounds of the Formula I are produced by the process (1), (2), (3) or (4), and if necessary, the non-quaternized compounds among them may be successively treated with an alkylating agent or a quaternizing agent to obtain the corresponding quaternized product.

As the alkylating agent or the quaternizing agent, all of known alkylating agents or quaternizing agents may be used. Examples of those agents are as follows:

Esters such as
  dimethyl sulfate
  dimethyl sulfate
  methyl p-toluenesulfonate
  methyl benzenesulfonate,
  etc.
Halogenated alkyls such as
  methyl iodide
  methyl bromide
  ethyl bromide, etc.
Acrylic acid derivatives such as
  acrylonitrile
  acrylamide
  methyl acrylate, etc.

The alkylation or quaternization is usually carried out at a temperature of 0° to 200° C. The reaction may be effected by directly adding an alkylating or a quaternizing agent to the reaction mixture after the previous processes (1) to (4). Alternatively, the compound obtained in the previous processes (1) to (4) may be recovered and then dispersed or dissolved in a fresh solvent to effect the alkylation or quaternization.

The compounds of the Formulas II, VII and IX used in the above-mentioned processes (1) to (4) are all novel compounds which can be easily produced by reacting the corresponding naphthalic anhydride with the corresponding hydrazine compound in the presence or absence of a solvent.

All of the novel naphthalimide derivatives thus obtained according to the present invention may be used as a valuable optical brightening agent. According to the conventional method, the present compound may be fixed onto or dispersed in fibrous materials or resinous materials consisting of polyester, polyacrylonitrile, polyamide, polyether, polyolefin, polyimide, polyvinyl chloride, polyvinylidene chloride, polyvinyl acetate, acryl, methacryl, epoxy, cellulose ester, cellulose ether, polyvinyl alcohol, polystyrene, polyurethane, polycarbonate, polyacetal, ABS polymer or alkyd, phenol, xylene, urea, melamine, coumarone-indene, silicone or fluorine-containing resin, and the resulting materials show a strong fluorescent of violet to blue under daylight or ultraviolet ray.

A method for optically brightening fibers with the present compounds will be explained below in more detail.

The optical brightening of fibers is advantageously carried out in an aqueous solution or dispersion. For example, fibers are dipped in an aqueous solution for dispersion of the preset compounds with heating so that the compounds may be absorbed by the fibers (dip dyeing method). Alternatively, fibers are dipped in an aqueous solution or dispersion of the present compounds till a certain amount of the compounds are exhausted and are then dried and heated to a temperature of 100° C. or higher to be fixed onto the fibers (thermosol method). An appropriate surface active agent, a carrier, other auxiliary agents or additives as well as an oxidizing agent, a bleaching agent, etc. may be added to accomplish the object of the present invention effectively. Also, if desired, the optical brightening may be carried out in combination with resin finishing, dyeing, etc.

The preent compounds are so stable to heat that they may be applied to so-called dope dyeing method, that is, by adding the present compounds to a molten polymeric material before spinning.

The present compounds can be also applied to various plastics other than fibers to produce a remarkable brightening effect. Concretely, the compunds may be applied by known methods such as dry blend method, master powder method, masterbatch method, coating method, etc. Also, optically brightened polymer materials can be produced by adding the present compounds alone or in admixture with various additives to the reaction mixture during the polymerization of a prepolymer or the copolymerization.

As described above, the present compounds are very useful in the optical brightenng of organic polymer materials. The optical brightening can be sufficiently accomplished by using a very small amount such as 0.001 to 0.05% of the present compounds based on the material to be brightened. Of course, a further excellent effect can be expected if a laerger amount of the present compounds are used.

As is clear from the above description, the optical brightening with the present compounds may be carried out at any stage, that is, before, during or after the forming of organic polymer materials.

The following examples will serve to illustrate the practice of the present invention in more detail but should not be construed to limit the scope of the invention.

In these examples, all parts are expressed by weight unless otherwise indicated.

EXAMPLE 1

To 1,000 parts by volume of acetic acid, 66.6 parts of N-amino-4-methoxynaphthalimide was added. Further 66.9 parts of potassium cyanate was added and the mixture was stirred for three hours at room temperature. The separated crystals were recovered by filtration, and washed with a small amount of acetic acid and then with water, and were then dried. Thus, 56.3 parts of N-ureido-4-methoxynaphthalimide represented by the formula,

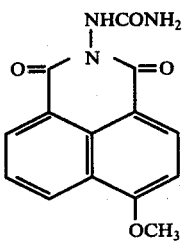

having a melting point of 303° to 305° C. was obtained.

EXAMPLE 2

To a suspension of 24.2 parts of N-amino-4-methoxynaphthalimide in 500 parts by volume of toluene, 11.4 parts of methyl isocyanate was added. The mixture was stirred for 8 hours at 70° to 80° C. and then cooled to room temperature. The separated crystals were recovered by filtration, and washed with toluene and then with methanol, and were then dried. Thus, 26.9 parts of N-(3-methylureido)-4-methoxynaphtahlimide represented by the formula,

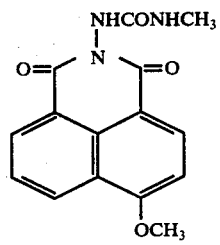

having a melting point of 300° to 301° C. was obtained.

The following compounds were produced by reacting the compounds of the Formula Ii with isocyanic acid derivatives as indicated below in the same manner as in Example 2.

| Ex. No. | Formula II R | R₁ | Isocyanic acid derivative | Product | Melting Point (° C.) |
|---|---|---|---|---|---|
| 3 | CH₃ | H | Phenyl isocyanate | 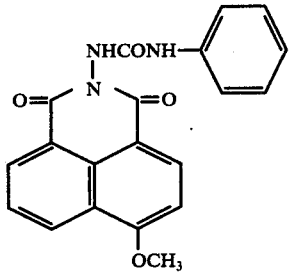 | 310–312 |
| 4 | C₂H₅ | CH₃ | Methyl isocyanate | 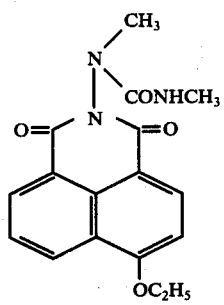 | 264–265 |
| 5 | CH₃ | H | Xylylene diisocyanate | 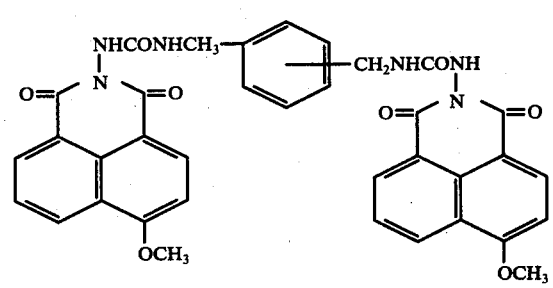 | 260–261 |
| 6 | CH₃ | H | Hexamethylene diisocyanate | 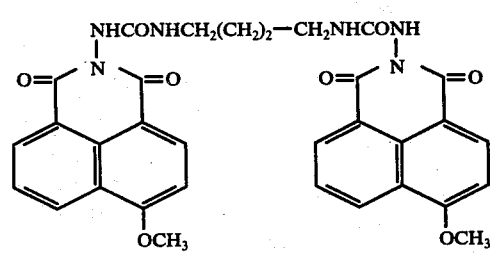 | 231–235 |

-continued

| Ex. No. | Formula II R | R₁ | Isocyanic acid derivative | Product | Melting Point (° C.) |
|---|---|---|---|---|---|
| 7 | (phenyl) | H | Methyl isocyanate | (naphthalimide with N-NHCONHCH₃ and 4-phenoxy substituent) | 140-143 |

EXAMPLE 8

Into a suspension of 2.0 parts of N-methylamino-4-methoxynaphthalimide in 20 parts of acetone, 1.8 parts of o-toluyl chloride was added. The mixture was stirred for 20 hours at room temperature and was then concentrated under reduced pressure. The residue was recrystallized from ethanol. Thus, 2.2 parts of N-(methyl-o-toluylamino)-4-methoxynaphthalimide represented by the formula,

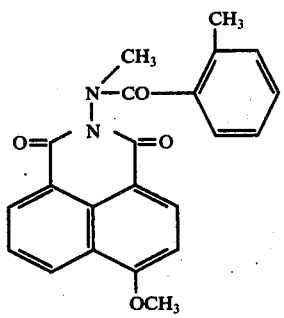

having a melting point of 179° to 180° C. was obtained.

The following compounds were produced by reacting the compounds of the Formula II with acid halides as indicated below in the same manner as in Example 8.

| Example No. | Formula II R | R₁ | Acid halide | Formula I R | R₁ | Y | R₂ (or R₄) | Melting point (°C) |
|---|---|---|---|---|---|---|---|---|
| 9 | CH₃ | H | Acetyl chloride | CH₃ | H | CO | CH₃ | 257–259 |
| 10 | CH₃ | H | Acetyl bromide | CH₃ | H | CO | CH₃ | 257–259 |
| 11 | CH₃ | H | Benzoyl chloride | CH₃ | H | CO | phenyl | 226–227 |
| 12 | CH₃ | H | Terephthaloyl chloride | CH₃ | H | CO | p-substituted phenyl | >300 |
| 13 | CH₃ | H | p-Toluyl chloride | CH₃ | H | CO | p-tolyl | 228–230 |
| 14 | CH₃ | H | o-Chlorobenzoyl chloride | CH₃ | H | CO | o-chlorophenyl | 210–212 |
| 15 | CH₃ | H | p-Chlorobenzoyl chloride | CH₃ | H | CO | p-chlorophenyl | 254–255 |
| 16 | CH₃ | H | Trimellitic acid chloride | CH₃ | H | CO | trimellitic anhydride residue | >300 |
| 17 | CH₃ | H | Chloroacetyl chloride | CH₃ | H | CO | —CH₂Cl | 237–23 |
| 18 | C₂H₅ | H | Acetyl chloride | C₂H₅ | H | CO | CH₃ | 251–25 |
| 19 | C₂H₅ | H | Benzoyl chloride | C₂H₅ | H | CO | phenyl | 203–205 |

-continued

| Example No. | Formula II R | Formula II R₁ | Acid halide | Formula I R | Formula I R₁ | Formula I Y | Formula I R₂ (or R₄) | Melting point (°C.) |
|---|---|---|---|---|---|---|---|---|
| 20 | phenyl | H | Acetyl bromide | phenyl | H | CO | $CH_3$ | 137–140 |
| 21 | Same as above | H | Benzoyl chloride | Same as above | H | CO | phenyl | 216–218 |
| 22 | " | H | Chloroacetyl chloride | " | H | CO | $CH_2Cl$ | 192–193 |
| 23 | $-CH_2CH_2-O-C_4H_9$ | H | Acetyl chloride | $-CH_2CH_2-O-C_4H_9$ | H | CO | $CH_3$ | 138–140 |
| 24 | Same as above | H | Benzoyl chloride | Same as above | H | CO | phenyl | 179 |
| 25 | $CH_3$ | H | Ethyl chloroformate | $CH_3$ | H | COO | $C_2H_5$ | 223–226 |
| 26 | $CH_3$ | H | Phenyl chloroformate | $CH_3$ | H | COO | phenyl | >300 |
| 27 | $CH_3$ | $CH_3$ | " | $CH_3$ | $CH_3$ | COO | Same as above | 194–195 |
| 28 | $CH_3$ | H | Tosyl chloride | $CH_3$ | H | $SO_2$ | p-tolyl ($CH_3$) | 265–266 |
| 29 | $C_2H_5$ | $CH_3$ | " | $C_2H_5$ | $CH_3$ | $SO_2$ | p-tolyl ($CH_3$) | 304–307 |
| 30 | $CH_3$ | H | Dimethylcarbamoyl chloride | $CH_3$ | H | $-CON-CH_3$ | $CH_3$ | 271–272 |
| 31 | $C_2H_5$ | H | Chloroacetyl chloride | $C_2H_5$ | H | CO | $CH_2Cl$ | 247–249 |
| 32 | $CH_2CH_2OC_4H_9$ | H | Chloroacetyl chloride | $CH_2CH_2OC_4H_9$ | H | CO | $CH_2Cl$ | 160–161 |

-continued

| Example No. | Formula II R | Formula II R₁ | Acid halide | Formula I R | Formula I R₁ | Formula I Y | Formula I R₂ (or R₄) | Melting point (°C.) |
|---|---|---|---|---|---|---|---|---|
| 33 | CH₃ | CH₃ | Acetyl chloride | CH₃ | CH₃ | CO | CH₃ | 245-246 |
| 34 | CH₃ | CH₃ | Benzoyl chloride | CH₃ | CH₃ | CO |  | 141-142 |
| 35 | CH₃ | CH₃ | m-Toluyl chloride | CH₃ | CH₃ | CO | 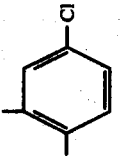 | 145-146 |
| 36 | CH₃ | CH₃ | p-Chlorobenzoyl chloride | CH₃ | CH₃ | CO | 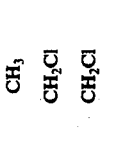 | 170-172 |
| 37 | CH₃ | CH₃ | 2,4-dichlorobenzoyl chloride | CH₃ | CH₃ | CO | 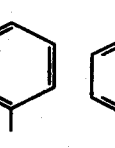 | 214-215 |
| 38 | CH₃ | CH₃ | Chloroacetyl chloride | CH₃ | CH₃ | CO | CH₂Cl | 110-113 |
| 39 | C₂H₅ | CH₃ | Acetyl chloride | C₂H₅ | CH₃ | CO | CH₃ | 171-172 |
| 40 | C₂H₅ | CH₃ | Chloroacetyl chloride | C₂H₅ | CH₃ | CO | CH₂Cl | 170-172 |
| 41 | C₂H₅ | CH₃ | " | C₂H₅ | C₂H₅ | CO | CH₂Cl | 118-120 |
| 42 | CH₃ | CH₂CH₂OH | Benzoyl chloride | CH₃ | CH₂CH₂OH | CO | | 180-182 |
| 43 | C₂H₅ | CH₃ | " | C₂H₅ | CH₃ | CO | 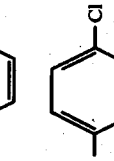 | 145-147 |
| 44 | C₂H₅ | CH₃ | p-Chlorobenzoyl chloride | C₂H₅ | CH₃ | CO |  | 190-191 |

-continued

| Example No. | Formula II R | Formula II R$_1$ | Acid halide | Formula I R | Formula I R$_1$ | Formula I Y | Formula I R$_2$ (or R$_4$) | Melting point (° C.) |
|---|---|---|---|---|---|---|---|---|
| 45 | C$_2$H$_5$ | CH$_3$ | 2,4-dichlorobenzoyl chloride | C$_2$H$_5$ | CH$_3$ | CO | 2,4-dichlorophenyl | 201-203 |
| 46 | C$_2$H$_5$ | CH$_3$ | o-Toluyl chloride | C$_2$H$_5$ | CH$_3$ | CO | o-tolyl (CH$_3$) | 175-176 |
| 47 | C$_2$H$_5$ | CH$_3$ | m-Toluyl chloride | C$_2$H$_5$ | CH$_3$ | CO | m-tolyl (CH$_3$) | 172-173 |
| 48 | CH$_3$ | C$_2$H$_5$ | Acetyl chloride | CH$_3$ | C$_2$H$_5$ | CO | CH$_3$ | 158-160 |
| 49 | CH$_3$ | C$_2$H$_5$ | Benzoyl chloride | CH$_3$ | C$_2$H$_5$ | CO | phenyl | 130-132 |
| 50 | C$_2$H$_5$ | C$_2$H$_5$ | Acetyl chloride | C$_2$H$_5$ | C$_2$H$_5$ | CO | CH$_3$ | 137-139 |
| 51 | C$_2$H$_5$ | C$_2$H$_5$ | Benzoyl chloride | C$_2$H$_5$ | C$_2$H$_5$ | CO | phenyl | 131-132 |
| 52 | CH$_3$ | CH$_3$ | Acetyl chloride | phenyl | CH$_3$ | CO | CH$_3$ | 157-160 |
| 53 | CH$_2$CH$_2$OCH$_2$ | CH$_3$ | " | CH$_2$CH$_2$OCH$_3$ | CH$_3$ | CO | CH$_3$ | 130 |

EXAMPLE 54

To 300 parts by volume of toluene, 20 parts of N-amino-4-ethoxynaphthalimide was added. Further, 24 parts of acetic anhydride was added, and the mixture was stirred for 5 hours at room temperature. The separated crystals were recovered by filtration, washed with 300 parts by volume of toluene and dried. Thus, 22.6 parts of a compound represented by the formula,

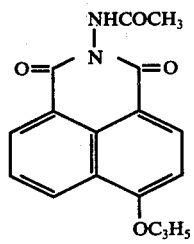

was obtained. The product showed a melting point of 248° to 249° C. and the wave length of maximum ultraviolet absorption in ethanol solution thereof showing blue fluorescence was 367 mµ.

The following compounds of the general formula,

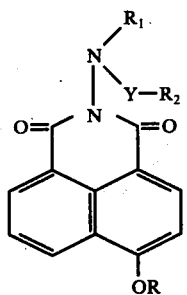

where obtained by reacting the compounds of the Formula II with acid anhydrides as indicated below in the same manner as in Example 54.

mide was added. The mixture was heated to 190° C. in 10 minutes and kept at 185° to 195° C. for one hour. The mixture was then allowed to cool to room temperature. 10,000 parts of water was added and the mixture was heated and then filtered while hot. The cake was washed with hot water and dried. The product was then recrystallized from acetic acid. Thus, 81.5 parts of a compound represented by the formula,

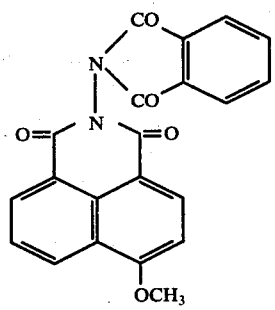

was obtained. The product has a melting point of 310° to 312° C. and showed blue fluorescence. The wavelength of maximum ultraviolet absorption in ethanol solution thereof was 366 mµ.

The following compounds of the general formula,

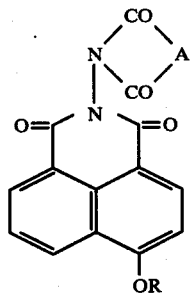

were produced by reacting the compounds of the Formula II wherein $R_1$ is hydrogen with acid anhydrides an indicated below in the same manner as in Example 64.

| Example Number | Formula II R | $R_1$ | Acid anhydride | Above formula R | $R_1$ | Y | $R_2$ | Melting point (° C.) |
|---|---|---|---|---|---|---|---|---|
| 55 | $CH_3$ | H | Acetic anhydride | $CH_3$ | H | CO | $CH_3$ | 257–259 |
| 56 | $CH_3$ | H | Benzoic anhydride | $CH_3$ | H | CO | ⌬ | 226–227 |
| 57 | ⌬ | H | Acetic anhydride | ⌬ | H | CO | $CH_3$ | 137–140 |
| 58 | $CH_2CH_2OC_4H_9$ | H | " | $CH_2CH_2OC_4H_9$ | H | CO | $CH_3$ | 138–140 |
| 59 | $CH_3$ | $CH_3$ | " | $CH_3$ | $CH_3$ | CO | $CH_3$ | 245–246 |
| 60 | $C_2H_5$ | $CH_3$ | " | $C_2H_5$ | $CH_3$ | CO | $CH_3$ | 171–172 |
| 61 | $CH_3$ | $C_2H_5$ | " | $CH_3$ | $C_2H_5$ | CO | $CH_3$ | 158–160 |
| 62 | $C_2H_5$ | $C_2H_5$ | " | $C_2H_5$ | $C_2H_5$ | CO | $CH_3$ | 137–139 |
| 63 | $CH_2CH_2OCH_3$ | $CH_3$ | " | $CH_2CH_2OCH_3$ | $CH_3$ | CO | $CH_3$ | 130 |

EXAMPLE 64

500 parts of phthalic anhydride was molten at 140° C., to which 78.7 parts of N-amino-4-methoxynaphthali-

| Example number | R in Formula II | Acid anhydride | Above formula R | A | Melting point (° C.) |
|---|---|---|---|---|---|
| 65 | CH$_3$ | Dichlorophthalic anhydride | CH$_3$ | 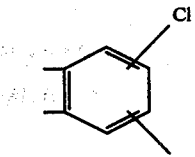 | >300 |
| 66 | CH$_3$ | Tetrachlorophthalic anhydride | CH$_3$ | 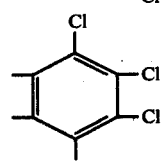 | >300 |
| 67 | CH$_3$ | Tetrabromophthalic anhydride | CH$_3$ | 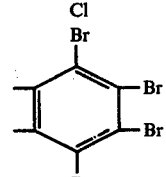 | >300 |
| 68 | CH$_3$ | Napthalic anhydride | CH$_3$ | 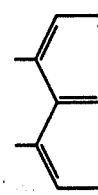 | >300 |
| 69 | CH$_3$ | Maleic anhydride | CH$_3$ | —CH=CH— | 268–272 |
| 70 | CH$_3$ | Succinic anhydride | CH$_3$ | —CH$_2$—CH$_2$— | 251–253 |
| 71 | CH$_2$CH$_2$OC$_4$H$_9$ | Phthalic anhydride | CH$_2$CH$_2$OC$_4$H$_9$ |  | 201–203 |

EXAMPLE 72

A mixture of 3.7 parts of N-(methylbenzoylamino)-4-chloronaphthalimide, 20 parts of ethanol and 0.6 part of potassium hydroxide was heated for 10 hours under reflux. The mixture was then allowed to cool to room temperature and a small amount of water was added thereto. The separated crystals were recovered by filtration, washed with water and dried. Thus, N-(methylbenzoylamino)-4-ethoxynaphthalimide represented by the formula,

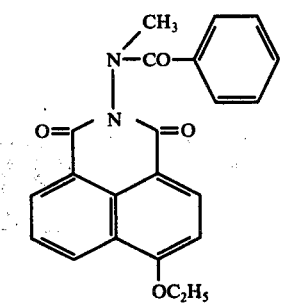

having a melting point 145° to 147° C. was obtained.

The following compounds were produced by reacting the compounds of the Formula VII with the compounds of the Formula VIII in the same manner as in Example 72.

| Example number | Formula VII R₁ | R₂ | X | Formula VIII | Product | Elementary analysis N (percent) Found | Calcd. |
|---|---|---|---|---|---|---|---|
| 73 | CH₃ | CH₃ | Cl | CH₃OH | [structure with OCH₃] | 9.39 | 9.26 |
| 74 | CH₃ | CH₃ | Cl | C₂H₅OH | [structure with OC₂H₅] | 8.52 | 8.53 |
| 75 | CH₃ | C₆H₁₁ | Br | CH₃OCH₂CH₂OH | [structure with OCH₂CH₂OCH₃] | 6.82 | 6.7 |
| 76 | CH₂OCH₂CH₂O— [phenyl] | | Cl | [phenyl]CH₂OH | [structure with OCH₂-phenyl] | 5.83 | 5.81 |
| 77 | CH₃ | Same as above. | Br | [phenyl]OH | [structure with O-phenyl] | 6.63 | 6.58 |

-continued

| Example number | Formula VII R₁ | R₂ | X | Formula VIII | Product | Elementary analysis N (percent) Found | Calcd. |
|---|---|---|---|---|---|---|---|
| 78 | CH₃ | (phenyl) | Br | CH₃—(phenyl)—OH | (structure with N-CH₃, N-COC₆H₅, naphthalimide with O-tolyl) | 6.42 | 6.29 |
| 79 | CH₃ | CH₃ | Cl | (C₂H₅)₂N—CH₂CH₂OH | (structure with N-CH₃, N-COCH₃, naphthalimide with OCH₂CH₂N(C₂H₅)₂) | 10.96 | 10.92 |

EXAMPLE 80

2.5 parts of N-acetylamino-4-hydroxynaphthalimide (M.P. 306° to 307° C.) was dissolved in an aqueous solution of 3.0 parts of sodium hydroxide in 20 parts of water and 5 parts by volume of methanol was added thereto. The mixture was cooled to 10° C. 3.7 parts of dimethyl sulfate was gradually dropped into the mixture in 5 hours. After the completion of dropping, the mixture was stirred for 5 hours at room temperature and was then acidified strongly with hydrochloric acid. The separated crystals were recovered by filtration and were then recrystallized from glacial acetic acid. Thus, N-acetylamino-4-methoxynaphthalimide represented by the formula,

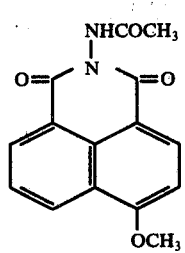

having a melting point of 257° to 259° C. was obtained.

The following compounds were obtained by reacting the compounds of the Formula IX with alkylating agents as indicated below in the same manner as in Example 80.

| Ex. No. | X in formula IX | Alkylating agent | Product |
|---|---|---|---|
| 81 | —N(C₂H₅)(COCH₃) | (C₂H₅)₂SO₄ | (naphthalimide with N-N(C₂H₅)(COCH₃) and OC₂H₅) |

-continued

| Ex. No. | X in formula IX | Alkylating agent | Product |
|---|---|---|---|
| 82 | -N(CH₃)COCH₃ | C₆H₅-CH₂Cl | (structure with N(CH₃)COCH₃ and OCH₂C₆H₅) |
| 83 | -N(CH₃)CO-C₆H₅ | CH₃-CH-CH₃ with O (propylene oxide) | (structure with OCH₂CH₂OH) |
| 84 | -N(CH₃)CO-C₆H₄-CH₃ | CH₃-C₆H₄-SO₃-O-CH₂CH₂-OCH₃ | (structure with OCH₂CH₂OCH₃) |
| 85 | -NHCO-C₆H₅ | CH₃Br | (structure with NHCO-C₆H₅ and OCH₃) |

EXAMPLE 86

A mixture of 31.9 parts of N-chloroacetamido-4-methoxynaphthalimide, 300 parts of methanol and 120 parts of a 30% aqueous solution of trimethylamine was heated with stirring for 8 hours under reflux. Excess amount of trimethylamine and the solvent was removed by evaporation to dryness under reduced pressure. Thus, a compound represented by the formula,

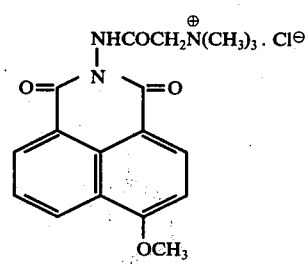

was obtained in a quantitative yield.

The wave length of maximum absorption in aqueous solution thereof was 376 mμ and the solution showed strong blue fluorescence under daylight and ultraviolet ray. Also, when polyacrylonitrile fibers were dyed with the product according to a usual method, remarkably brilliant white dyeings were obtained.

The wave length of maximum ultraviolet absorption ($\lambda_{max}$) of the compounds which were produced by reacting the compounds of the Formula X with tertiary nitrogen atom-containing amines or hydrazines in the same manner as in Example 86 and the color of fluorescence on polyacrylonitrile fibers obtained by dyeing the fibers with the respective compound according to a usual method are shown in the following table.

| Ex. No. | R | R₁ | R₅ | Z | Amine or hydrazine | $\lambda_{max}$ (mµ) | Color of fluorescence on polyacrylonitrile fibers |
|---|---|---|---|---|---|---|---|
| 87 | CH₃ | H | CH₂ | Cl | Pyridine | 378 | Blue. |
| 88 | CH₃ | H | CH₂ | Cl | Dimethylhydrazine | 378 | " |
| 89 | CH₃ | H | CH₂ | Cl | Triethylenediamine | 377 | " |
| 90 | CH₃ | CH₃ | CH₂ | Cl | Pyridine | 379 | " |
| 91 | CH₂ | CH₃ | CH₂ | Cl | Trimethylamine | 378 | " |
| 92 | CH₃ | CH₃ | CH₂ | Cl | Dimethylhydrazine | 379 | " |
| 93 | C₂H₅ | H | CH₂ | Cl | Trimethylamine | 379 | " |
| 94 | C₂H₅ | CH₂ | CH₃ | Cl | " | 379 | " |
| 95 | C₂H₅ | C₂H₅ | CH₂ | Cl | " | 375 | " |
| 96 | C₂H₅ | H | CH₂ | Cl | " | 370 | Reddish blue. |
| 97 | C₂H₅ | C₂H₅ | CH₂ | Cl | Picoline | 379 | Blue. |
| 98 | CH₃ | H | CH₂ | Cl | Triethylamine | 378 | " |
| 99 | CH₃ | CH₂CH₂OH | CH₂ | Cl | Diethanol-methylamine | 378 | " |
| 100 | CH₃ | CH₂CH₂OH | CH₂ | Cl | N-methylmorpholine | 378 | " |
| 101 | CH₃ | C₃H₇ | CH₂ | Cl | Triethylenediamine | 378 | " |
| 102 | CH₃ | C₄H₉ | CH₂CH₂ | Cl | Pyridine | 377 | " |
| 103 | CH₃ | CH₃ | CH₂CH₃ | Br | " | 379 | " |
| 104 | C₂H₅ | H | CH₂CH₂ | Cl | " | 378 | " |
| 105 | CH₃ | CH₃ | CH₂CHCH₂<br>\|<br>OH | Cl | " | 379 | " |
| 106 | CH₃ | CH₃ | CH=CH—CH₂ | Cl | " | 379 | " |
| 107 | CH₃ | CH₃ | ⟨benzyl -CH₂-⟩ | Cl | Trimethylamine | 379 | " |
| 108 | C₂H₅ | CH₃ | " | Cl | Pyridine | 378 | " |
| 109 | CH₃ | CH₃ | CH₂CH₂SO₂CH₂CH₂ | Cl | " | 379 | " |
| 110 | CH₃ | CH₃ | ⟨N-phenyl succinimide-CH⟩ | Cl | " | 379 | " |
| 111 | ⟨p-tolyl-CH₃⟩ | CH₃ | CH₂ | Cl | " | 371 | Reddish blue. |
| 112 | ⟨p-methoxyphenyl-OCH₃⟩ | H | CH₂ | Cl | " | 371 | " |
| 113 | CH₂CH₂OC₄H₉ | H | CH₂ | Cl | Trimethylamine | 378 | Blue. |
| 114 | CH₂CH₂OC₄H₉ | CH₃ | CH₂ | Cl | " | 379 | " |

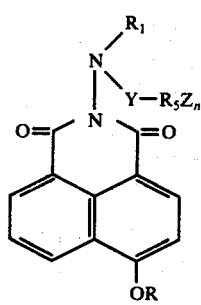

(X)

The wave length of maximum ultraviolet absorption ($\lambda_{max}$) of the compounds which were produced by reacting the compounds of the Formula XI with tertiary nitrogen atom-containing amines or hydrazines in the same manner as in Example 86 and the color of fluorescence on polyacrylonitrile fibers obtained by dyeing the fibers with the respective compound according to a usual method are shown in the following table.

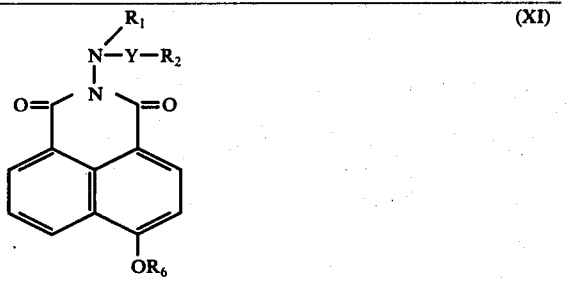

(XI)

| Example number: | In Formula XI (Y = CO) | | | Amine or hydrazine | $\lambda_{max}$ (mµ) | Color of fluorescence on polyacrylonitrile fibers |
|---|---|---|---|---|---|---|
| | $R_1$ | $R_2$ | $R_6$ | | | |
| 115 | $CH_3$ | $CH_3$ | $CH_2CHCH_2Cl$ <br> \| <br> $OH$ | Trimethylamine | 377 | Blue. |
| 116 | $CH_3$ | $CH_3$ | " | Pyridine | 377 | " |
| 117 | $CH_3$ | –C₆H₅ (phenyl) | " | Trimethylamine | 377 | " |

EXAMPLE 118

A mixture of 33.4 parts of N-(N'-methyl-N'-chloroacetylamino)-4-methoxynaphthalimide, 300 parts of toluene and 9.4 parts of aniline was stirred for one hour under reflux. The mixture was then concentrated to dryness under reduced pressure. The residue was recrystallized from glacial acetic acid. Thus, 30 parts of a compound represented by the formula,

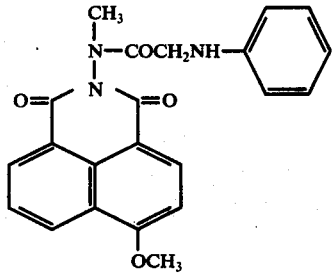

was obtained. An alcohol solution of this compound showed strong bluish violet fluorescence under daylight and ultraviolet ray.

The color of fluorescence of an alcohol solution of the compounds which were produced by reacting compounds of the Formula X with amines in the same manner as in Example 118 are shown in the following table.

| Example number | In formula X (Y = CO) | | | Amine | Color of fluorescence of alcohol solution |
|---|---|---|---|---|---|
| | R | $R_1$ | $R_5(Z)_n$ | | |
| 119 | $CH_3$ | $CH_3$ | $CH_2Cl$ | $n\text{-}C_4H_9NH_2$ | Bluish violet. |
| 120 | $CH_3$ | $CH_3$ | $CH_2Cl$ | $C_5H_{11}NH_3$ | " |
| 121 | $CH_3$ | H | $CH_2Cl$ | C₆H₅–CH₂NH₂ | ". |
| 122 | $CH_3$ | $C_2H_5$ | $CH_2Cl$ | Cl–C₆H₄–NH₂ | " |
| 123 | $CH_3$ | $C_2H_5$ | benzo-bis(=CCl)N,N | $NH_3$ | Blue. |

-continued

| Example number | R | R₁ | R₅(Z)ₙ | Amine | Color of fluorescence of alcohol solution |
|---|---|---|---|---|---|
| 124 | $CH_3$ | $C_3H_7$ | " | phenyl-$NH_2$ (aniline) | " |
| 125 | $CH_3$ | $C_4H_9$ | 1,4-dichlorophthalazine | $NH_3$ | " |
| 126 | $CH_3$ | $CH_3$ | " | phenyl-$NH_2$ (aniline) | " |
| 127 | $CH_3$ | $CH_3$ | 2,4-dichloro-5-methylpyrimidine | $NH_2$ | " |
| 128 | $CH_3$ | H | " | phenyl-$NH_2$ (aniline) | " |
| 129 | $CH_3$ | $CH_3$ | 4-($NHCOCH_2Cl$)-phenyl | $CH_3NH_2$ | Bluish violet. |
| 130 | $CH_3$ | $CH_3$ | N-(p-tolyl)-3,4-dichloromaleimide | $CH_3NH_2$ | " |
| 131 | $C_2H_5$ | $-CH_2CH_3OH$ | $CH_2Cl$ | phenyl-$NHNH_2$ | " |
| 132 | $C_2H_5$ | $CH_3$ | $CH_2Cl$ | $H_2N \cdot CH_2CH_2 \cdot NH_2$ | " |
| 133 | $CH_3$ | $CH_3$ | $CH_2Cl$ | $H_2N$-phenyl-$NH_2$ (p-phenylenediamine) | " |
| 134 | $CH_3$ | $CH_3$ | $CH_2Cl$ | $HN(C_2H_5)_2$ | " |
| 135 | $CH_3$ | H | $CH_2Cl$ | morpholine | " |
| 136 | $CH_3$ | H | $CH_2Cl$ | phenyl-$NHCH_3$ | " |

-continued

| Example number | R | R₁ | In formula X (Y = CO) R₅(Z)ₙ | Amine | Color of fluorescence of alcohol solution |
|---|---|---|---|---|---|
| 137 | CH₃ | H | ―⟨⟩―O―⟨⟩―NHCOCH₂Cl | HN(CH₃)₂ | " |
| 138 | CH₂CH₂OC₂H₅ | CH₃ | CH₂Cl | ⟨⟩―NH₂ | " |
| 139 | CH₃ | CH₃ | ⟨⟩―CH₂Cl | " | Blue. |
| 140 | C₂H₅ | CH₃ | " | " | " |
| 141 | CH₃ | CH₃ | ―⟨⟩―CH₂Cl | Cl―⟨⟩―NHNH₂ | " |
| 142 | CH₃ | CH₃ | " | HN(CH₂CH₃CN)₂ | " |

EXAMPLE 143

A mixture of 31.9 parts of N-chloroacetamide-4-methoxynaphthalimide, 300 parts of methanol and 22.5 parts of a 40% aqueous dimethylamine solution was stirred for 3 hours under reflux. The mixture was subjected to evaporation to dryness under reduced pressure. To the residue 300 parts of chlorobenzene was added and the mixture was heated to 100° C. 13.9 parts of dimethyl sulfate was dropped into the mixture. The mixture was then stirred at 100° C. for two hours, and was cooled to room temperature and filtered. The cake was washed with 300 parts of petroleum ether to obtain a compound of the formula,

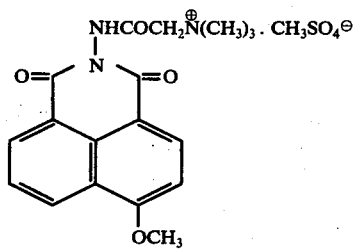

An aqueous solution of this compound had a wave length of maximum absorption of 376 mμ and showed strong fluorescence under daylight and ultraviolet ray.

Also, zinc chloride was added to the aqueous solution of the compound obtained above and the mixture was salted out to obtain a compound of the formula,

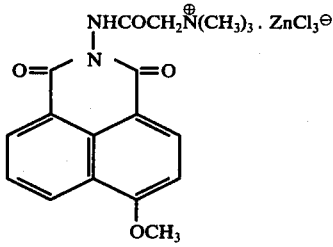

An aqueous solution of this compound had a wave length of maximum absorption of 376 mμ and showed strong fluorescence under daylight and ultraviolet ray.

When polyacrylonitrile fibers were dyed with the compound according to a usual method, remarkably brilliant white dyeings could be obtained.

The color of fluorescence on polyacrylonitrile fibers obtained by dyeing the fibers with the compounds which were produced by treating the compounds of the Formula X with secondary amines according to the same method as in Example 143 and then quaternizing the product with quaternizing agents is shown in the following table.

| Example number: | In Formula X n = 1, Y = CO | | | | Secondary amine | Quaternizing agent | Color of fluorescence on polyacrylonitrile fibers |
|---|---|---|---|---|---|---|---|
| | R | R₁ | R₅ | Z | | | |
| 144 | CH₃ | CH₃ | CH₃ | Cl | Dimethylamine | Methyl bromide | Blue. |
| 145 | CH₃ | H | CH₃ | Cl | " | Methyl p-toluene-sulfonate. | " |
| 146 | CH₃ | C₂H₅ | CH₃ | Cl | " | Acrylonitrile | " |
| 147 | CH₃ | CH₃ | CH₂ | Cl | Diethylamine | Methyl iodide | " |
| 148 | CH₃ | H | CH₂ | Cl | " | Ethyl bromide | " |
| 149 | CH₃ | H | CH₂ | Cl | Morpholine | Dimethyl sulfate | " |
| 150 | CH₃ | CH₃ | CH₂ | Cl | Pyrrolidine | " | " |
| 151 | CH₃ | CH₃ | CH₂ | Cl | N-methylaniline | " | " |
| 152 | CH₃ | CH₃ | CH₂ | Cl | Diethanolamine | " | " |

-continued

| Example number: | In Formula X n = 1, Y = CO | | | | Secondary amine | Quaternizing agent | Color of fluorescence on polyacrylonitrile fibers |
|---|---|---|---|---|---|---|---|
| | R | R₁ | R₅ | Z | | | |
| 153 | C₂H₅ | CH₃ | CH₂CH₂ | Br | Diethylamine | " | " |

EXAMPLE 154

Polyacrylonitrile fabric was dipped in a solution consisting of 0.08 part of a naphthalimide of the formula,

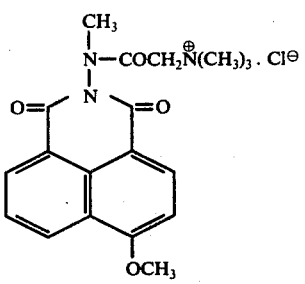

1.0 part of sodium chlorite, 0.4 part of a chlorine gas inhibitor and 1000 parts of water, which had been adjusted to pH of 3 to 4 with acetic acid, in a liquor ratio of 1:50. The solution was heated to the boil in 30 minutes and was then kept at the temperature for one hour. The thus dyed fabric was dipped in 1000 parts of a 0.2% aqueous sodium thiosulfate solution. The whole was heated at 60° to 70° C. for 20 minutes. The treated fabric was washed with water and dried to obtain a remarkably brilliant white fabric.

The color of fluorescence on polyacrylonitrile fabric obtained by dyeing the fabric with the following naphthalimide derivatives in the same manner as in Example 154 is shown below.

| Naphthalimide derivative | Color of fluor- on poly- acryloni- trile fabric |
|---|---|
| 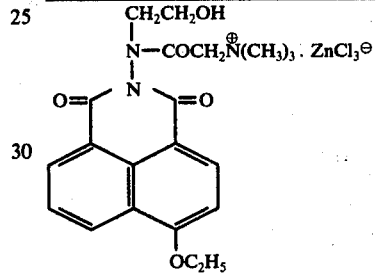 | Blue. |
| 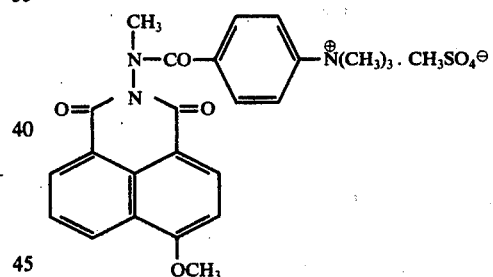 | " |

-continued

| Naphthalimide derivative | Color of fluor- on poly- acryloni- trile fabric |
|---|---|
| 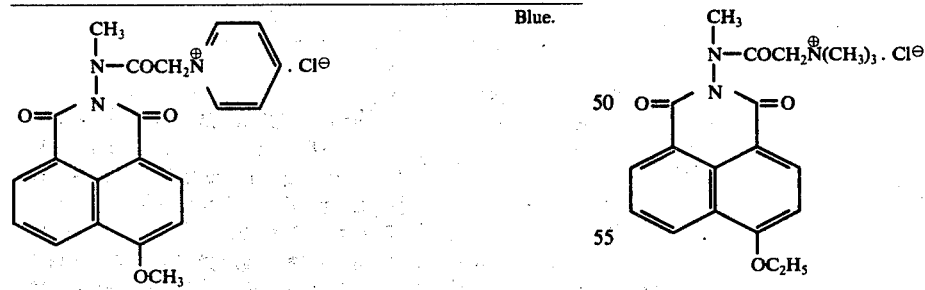 | " |
| | Bluish green. |
| | Reddish blue. |
| 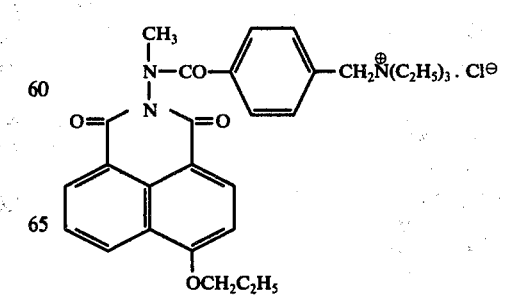 | Blue. |

| Naphthalimide derivative | Color of fluor- on poly- acryloni- trile fabric |
|---|---|
| 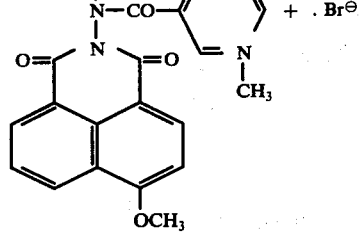 | Bluish green. |
| 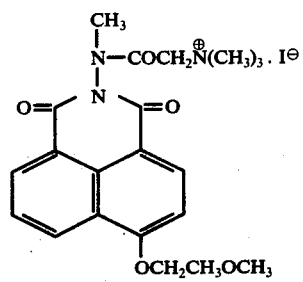 | Blue. |
| 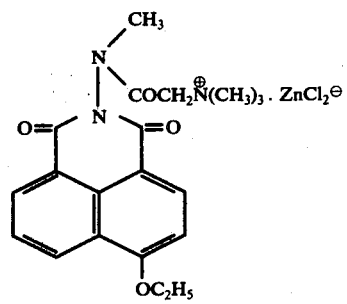 | " |
| 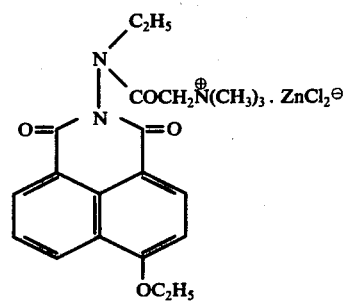 | " |
| 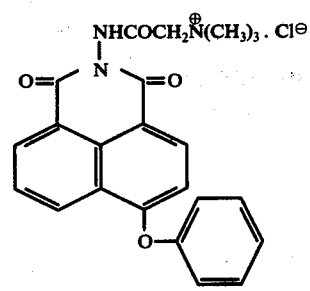 | Reddish blue. |

| Naphthalimide derivative | Color of fluor- on poly- acryloni- trile fabric |
|---|---|
|  | Blue. |
|  | " |
|  | " |

EXAMPLE 155

Polyacrylonitrile fabric was dipped in a dispersion consisting of 0.025 part of an N-acylaminonaphthalimide represented by the formula,

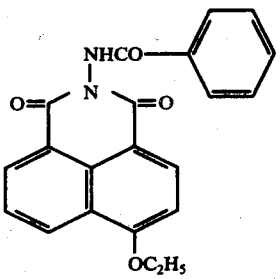

having a melting point of 202° to 205° C., 3 parts of Emulgen (a nonionic surface active agent) and 1000 parts of water in a liquor ratio of 1:60. The whole was heated to the boil in 30 minutes and kept at the temperature for one hour. The thus dyed fabric was then treated with a 3 g./l. aqueous Monogen (a sulfuric acid ester of a higher alcohol) solution at 90° C. for 15 minutes, washed with water and dried. Thus, a remarkably brilliant white dyeing was obtained.

In the same manner as described above, polyester, acetate and polyamide fibers could be also optically brightened.

EXAMPLE 156

Polyester fabric was dipped in an aqueous dispersion consisting of 0.1 part of an N-acylaminonaphthalimide represented by the formula,

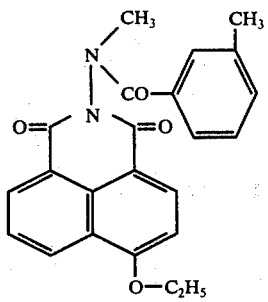

having a melting point of 172° to 173° C., 3 parts of Emulgen and 1000 parts of water, then squeezed by a mangle so that the weight increase might be 80%, and then subjected to padding. The padded fabric was then dried at 60° C. and was subjected to thermosol treatment at 200° C. for 30 seconds. Thus, a satisfactorily optically brightened fabric was obtained.

In the same manner as described above, acetate, polypropylene and nylon fibers could be optically brightened.

EXAMPLE 157

0.01 percent by weight of an N-acylaminonaphthalimide derivative represented by the formula,

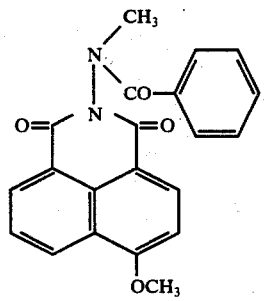

having a melting point of 141° to 142° C. was added to a polypropylene which had been molten at about 250° C. and they were well mixed with each other. The mixture was then subjected to melt spinning according to a usual method. Thus, a satisfactorily optically brightened fiber was obtained.

Also, when 0.5 part of titanium dioxide was further added to the above-mentioned melt and the mixture was then molded, an especially white molded article was obtained.

In the same manner as described above, a molded article of a high whiteness degree was obtained from ABS and polystyrene resins.

EXAMPLE 158

0.01 part of an N-acetylaminonaphthalimide derivative represented by the formula,

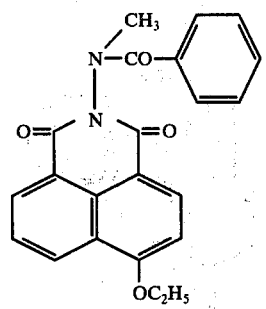

having a melting point of 145° to 147° C. was thoroughly mixed with 100 parts of soft polyvinyl chloride pellet containing a plasticizer, a stabilizer, etc. on a heated mixing mill at 150° C. The mixture was then formed into a desired molded article by casting, rolling or extruding.

The thus obtained molded article had a high transparency. Also, when 1 part of titanium dioxide was further added to the above-mentioned hot mixture, a molded article having a high whiteness degree was obtained.

What is claimed is:

1. A naphthalimide compound of the formula

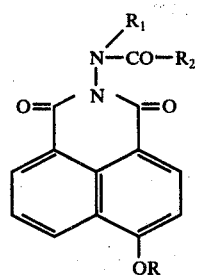

wherein
R is $C_1$-$C_6$ alkyl, benzyl, $C_1$-$C_6$ alkoxy-$C_1$-$C_6$ alkyl, or phenyl;
$R_1$ is hydrogen, $C_1$-$C_6$ alkyl, hydroxy-$C_1$-$C_6$ alkyl or $C_1$-$C_6$ alkoxy $C_1$-$C_6$ alkyl and
$R_2$ is $C_1$-$C_6$ alkyl, halo-$C_1$-$C_6$ alkyl, phenyl, or $C_1$-$C_6$-alkyl- or halogen-substituted-phenyl.

2. The naphthalimide compound of claim 1 wherein R is methyl, ethyl, methoxyethyl, butoxyethyl, benzyl or phenyl; $R_1$ is hydrogen, methyl, ethyl, methoxyethyl or hydroxyethyl and $R_2$ is methyl, hexyl, chloromethyl, phenyl, tolyl or chloro-phenyl.

3. A compound of the formula,

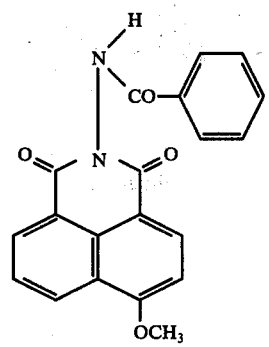

4. A compound of the formula,

5. A compound of the formula,
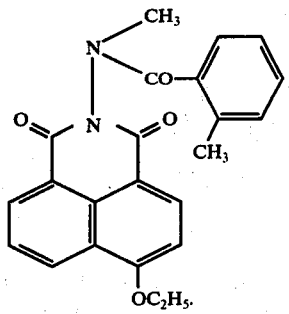
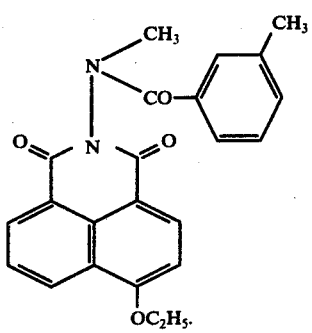
6. A naphthalimide compound of claim 1, wherein $R_1$ is methyl group.
7. A compound of the formula,
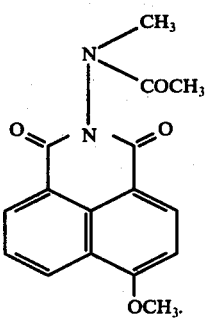
8. A compound of the formula,
9. A compound of the formula,
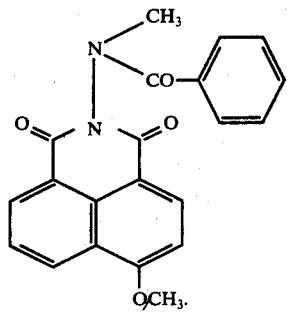
10. A compound of the formula,
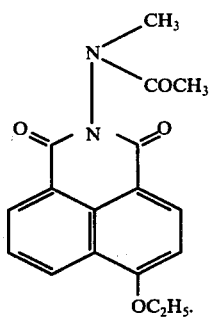
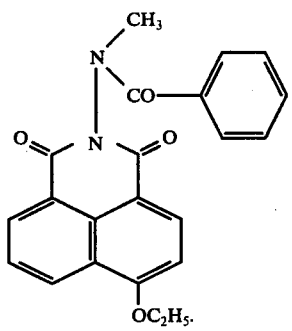
11. A compound of the formula,
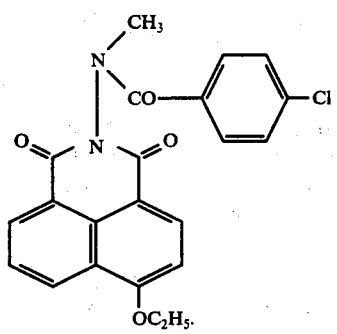
* * * * *